(12) United States Patent
Kregel et al.

(10) Patent No.: US 12,097,335 B2
(45) Date of Patent: Sep. 24, 2024

(54) CUSTOM LENGTH STYLET

(71) Applicant: Medtronic, Inc., Minneapolis, MN (US)

(72) Inventors: Elizabeth Kregel, Robbinsdale, MN (US); Thomas I. Miller, Blaine, MN (US); Jason Vargas, Villa, PR (US); Jayesh Patel, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 740 days.

(21) Appl. No.: 16/552,613

(22) Filed: Aug. 27, 2019

(65) Prior Publication Data

US 2021/0060294 A1    Mar. 4, 2021

(51) Int. Cl.
| | | |
|---|---|---|
| *A61N 1/05* | (2006.01) | |
| *A61B 17/34* | (2006.01) | |
| *A61B 17/50* | (2006.01) | |
| *A61M 25/01* | (2006.01) | |
| *A61M 25/09* | (2006.01) | |
| *A61N 1/375* | (2006.01) | |
| *A61B 17/00* | (2006.01) | |
| *A61N 1/04* | (2006.01) | |

(52) U.S. Cl.
CPC ...... *A61M 25/0102* (2013.01); *A61B 17/3468* (2013.01); *A61M 25/0905* (2013.01); *A61N 1/37518* (2017.08); *A61B 2017/00477* (2013.01); *A61B 2017/00831* (2013.01); *A61B 2017/00955* (2013.01); *A61M 25/09041* (2013.01); *A61N 1/0488* (2013.01); *A61N 1/05* (2013.01); *A61N 2001/0578* (2013.01)

(58) Field of Classification Search
CPC ...... A61B 17/3468; A61B 2017/00477; A61B 2017/00955; A61B 17/50; A61N 1/05–1/0597; A61M 25/09; A61M 25/02108; A61M 25/09116; A61M 25/09125; A61M 25/09133
USPC ........................................ 600/585; 606/129
See application file for complete search history.

(56) References Cited

U.S. PATENT DOCUMENTS

| | | | |
|---|---|---|---|
| 4,209,019 A | 6/1980 | Dutcher et al. | |
| 5,360,441 A | 11/1994 | Otten | |
| 5,843,153 A * | 12/1998 | Johnston | ................ A61N 1/056 600/585 |
| 8,721,659 B2 | 5/2014 | Bridgeman et al. | |
| 2013/0053865 A1* | 2/2013 | Bridgeman | .......... A61N 1/0551 29/505 |

(Continued)

*Primary Examiner* — Kathleen S Holwerda
(74) *Attorney, Agent, or Firm* — Husch Blackwell LLP

(57) ABSTRACT

A custom length stylet assembly for meeting medical device length tolerances. The custom length stylet assembly including a stylet wire having a length extending between a distal end and a proximal end, stylet handle defining a longitudinally oriented throughbore sized to retain a proximal portion of the stylet wire, the stylet handle further defining a proximately positioned track and tab, the track configured to retain a bent proximal end portion of the stylet wire, the length of the stylet wire selected during assembly of the stylet assembly to conform to the corresponding length of a body implantable lead within a predefined tolerance, the tab of the stylet handle melted into the track, thereby securely fastening stylet wire to the stylet handle to inhibit rotation or dislodgement.

20 Claims, 9 Drawing Sheets

(56) References Cited

U.S. PATENT DOCUMENTS

2013/0066331 A1* 3/2013 Chitre .................. A61N 1/0551
 606/129
2014/0330248 A1* 11/2014 Thompson-Nauman ....................
 A61M 5/14
 606/129

* cited by examiner

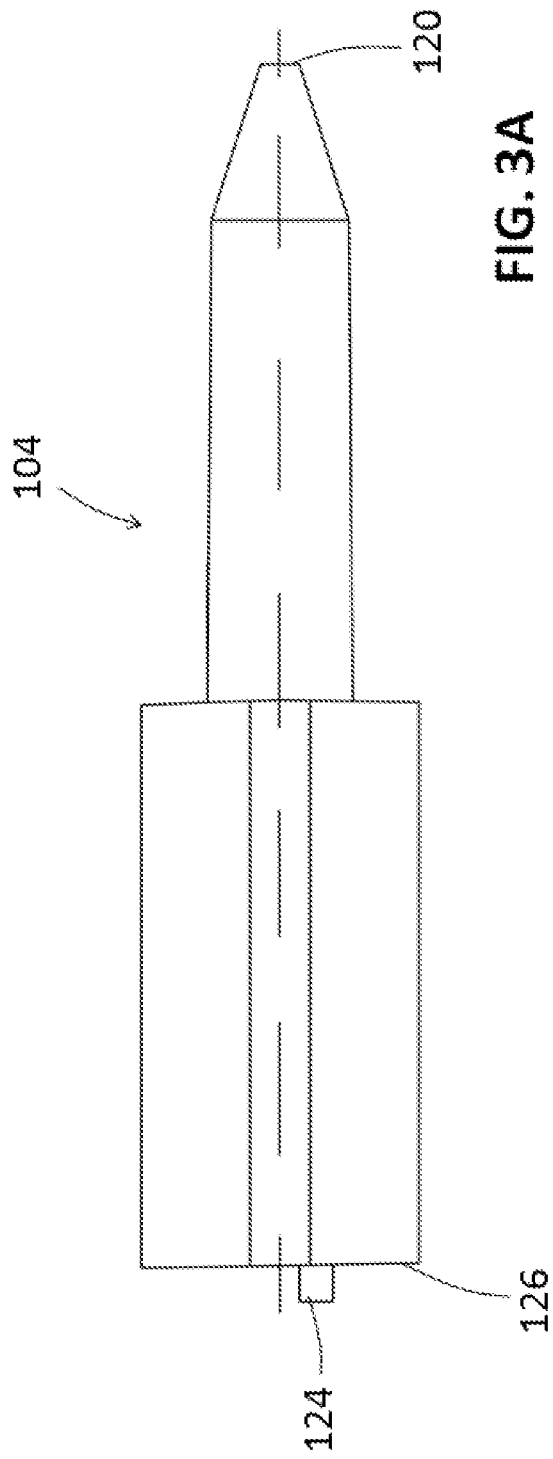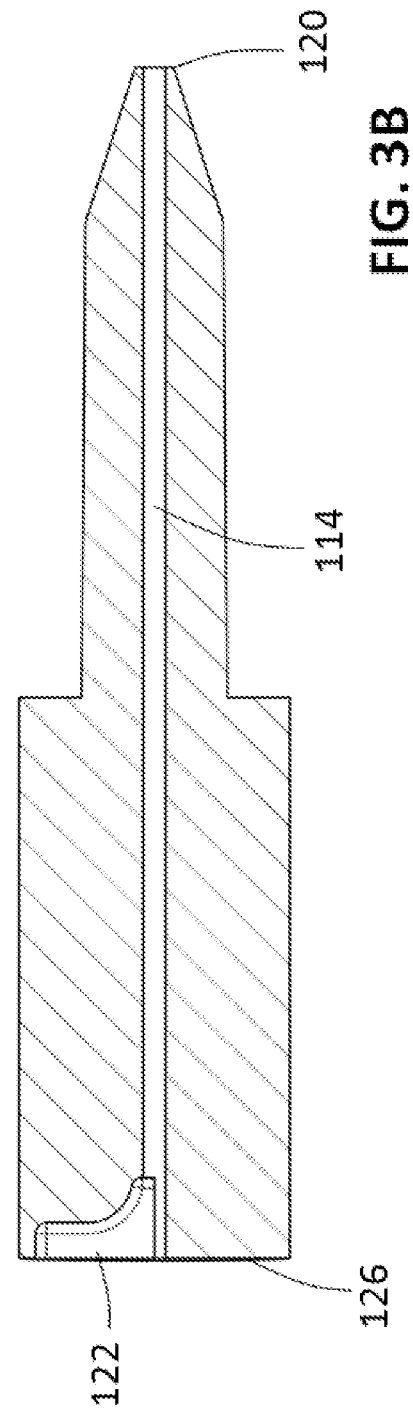

CUSTOM LENGTH STYLET

FIELD

The present technology is generally related to a wire guide or stylet assembly for the introduction of medical catheters or electrical leads to a desired site within a patient's body, and specifically to custom length stylets for meeting medical device length requirements and tolerances.

BACKGROUND

The state of art of implantable pulse generators for stimulating human tissue has advanced to the point that such devices are being designed and used in increasing numbers to treat a wide variety of medical conditions. In addition to implantable pulse generators for treating different types of cardiac conditions, so-called neurological pulse generators have been provided for stimulating a patient's nervous system in order to treat such diverse conditions such as pain, motor impairment, incontinence, and impotence, to name only a few.

In many cases, electrical stimulation pulses are conveyed from an implantable pulse generator to the desired stimulation site via an implantable lead having exposed electrodes at its distal end. In order to achieve the desired effects from delivery of a stimulating pulse, it is very important that the lead be properly positioned and stabilized in the patient, so that as much of the stimulating energy as possible is delivered to the appropriate site.

Stylets are commonly used for guiding and properly placing the implantable leads. Such stylets typically include a stiff wire, which is utilized to provide stability to the implantable lead during insertion into the body, often through a Touhy needle, and to provide the required stiffness necessary to guide the implantable lead to the area of desired placement. Stylet wires are manufactured and sold with specific dimensions, as well as specific materials dependent upon their intended use (pelvic nerve lead placement, intrathecal lead placement, intracranial access, etc.).

Where the stylet wire is to be paired with a specific type of implantable lead, the stylet wire must be manufactured to a specific length, generally within a given tolerance. In practice, matching the length of a stylet wire to an implantable lead within the given tolerance can be a difficult endeavor; particularly where components of the stylet and implantable lead are manufactured at separate facilities. The difficulty is compounded where the implantable leads are produced in a variety of lengths, or have lengths custom tailored to specific applications. Where length tolerances cannot be met, one or more of the stylets and/or implantable leads may be deemed unusable, thereby representing a yield loss in manufacturing.

The present disclosure addresses this concern.

SUMMARY

The techniques of this disclosure relate to custom length stylets and methods of use and manufacturing of custom length stylets which meet medical device length requirements and tolerances, and which avoid manufacturing yield losses.

In one aspect, the present disclosure provides a stylet wire assembly for use in positioning a body implantable lead. The stylet assembly can include a stylet wire configured to extend through a lumen of the body implantable lead, the stylet wire having a length extending between a distal end and a proximal end. The stylet assembly can further include a stylet handle configured to serve as a user grip from manipulation of the stylet wire. The stylet handle can define a longitudinally oriented throughbore size to retain a proximal portion of the stylet wire, such that a distal portion of the stylet wire extends distally from a distal end of the stylet handle. The stylet handle can further define a proximally positioned track and tab, the track can be configured to retain a bent proximal end portion of the stylet wire. The length of the stylet wire can be selected during assembly of the stylet assembly to conform to a corresponding length of the body implantable lead within a predefined tolerance. The tab of the stylet handle can be melted into the track, thereby securely fastening the stylet wire to the stylet handle and inhibiting rotation of the stylet wire relative to stylet handle.

In another aspect, the disclosure provides a lead kit for the insertion and positioning of an implantable neurostimulator lead into a body of the patient. The lead kit can include an implantable neurostimulator lead having a proximal end configured to be operably coupled to a medical device and a distal end to be positioned in communication with body tissue of the patient for electrical stimulation thereof. The implantable neurostimulator lead can include an electrical conductor extending between the proximal end and the distal end of the implantable neurostimulator lead. The implantable neurostimulator lead can further include an electrode head affixed to the distal end having one or more electrodes in communication with the electrical conductor, the electrode head can be configured to be exposed to the body tissue for the supply of electrical impulses thereto. The implantable neurostimulator lead can further include a body defining a longitudinally oriented lumen extending between the proximal end and a lumen termination point in proximity to the distal end. The lead kit can further include a stylet assembly for use in positioning the implantable neurostimulator lead into the body of the patient. The stylet assembly can include a stylet wire configured to extend through the lumen of the implantable neurostimulator lead, the stylet wire having a length extending between a distal end and a proximal end. The stylet assembly can further include a stylet handle configured to serve as a user grip for manipulation of the stylet wire. The stylet handle can define a longitudinally oriented throughbore sized to retain a proximal portion of the stylet wire, such that a distal portion of the stylet wire extends distally from a distal end of the stylet handle. The stylet handle can further define a proximally positioned tracking tab, the track configured to retain a bent proximal end portion of the stylet wire. The length of the stylet wire can be selected during assembly of the stylet assembly to conform to a corresponding length of the body and implantable neurostimulator lead within a predefined tolerance. The tab of the stylet handle can be melted into the track, thereby securely fastening the stylet wire to the stylet handle and inhibiting rotation of the stylet wire relative to stylet handle.

In another aspect, the disclosure provides a method of assembling the stylet assembly, including the steps of: forming a stylet handle defining a longitudinally oriented throughbore, a proximally positioned track and a proximally position tab; bending a proximal end portion of the stylet wire; cutting a stylet wire to conform to a corresponding length of a body implantable lead within a predefined tolerance; positioning the stylet wire within a longitudinally oriented throughbore defined in the stylet handle, such that the bent proximal end portion of the stylet wire is retained with the track and a distal portion of the stylet wire extends distally from a distal end of the stylet handle; and melting a proximately positioned tab of the stylet handle into the proximally positioned track, thereby securely fastening the stylet wire to the stylet handle and inhibiting rotation of the stylet wire relative to the stylet handle.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The disclosure can be more completely understood in consideration of the following detailed description of various embodiments of the disclosure, in connection with the accompanying drawings, in which:

FIG. 3A is a profile view depicting a stylet handle, in accordance with an embodiment of the disclosure.

FIG. 3B is cross-sectional view depicting the stylet handle of FIG. 3A.

Figure 1:
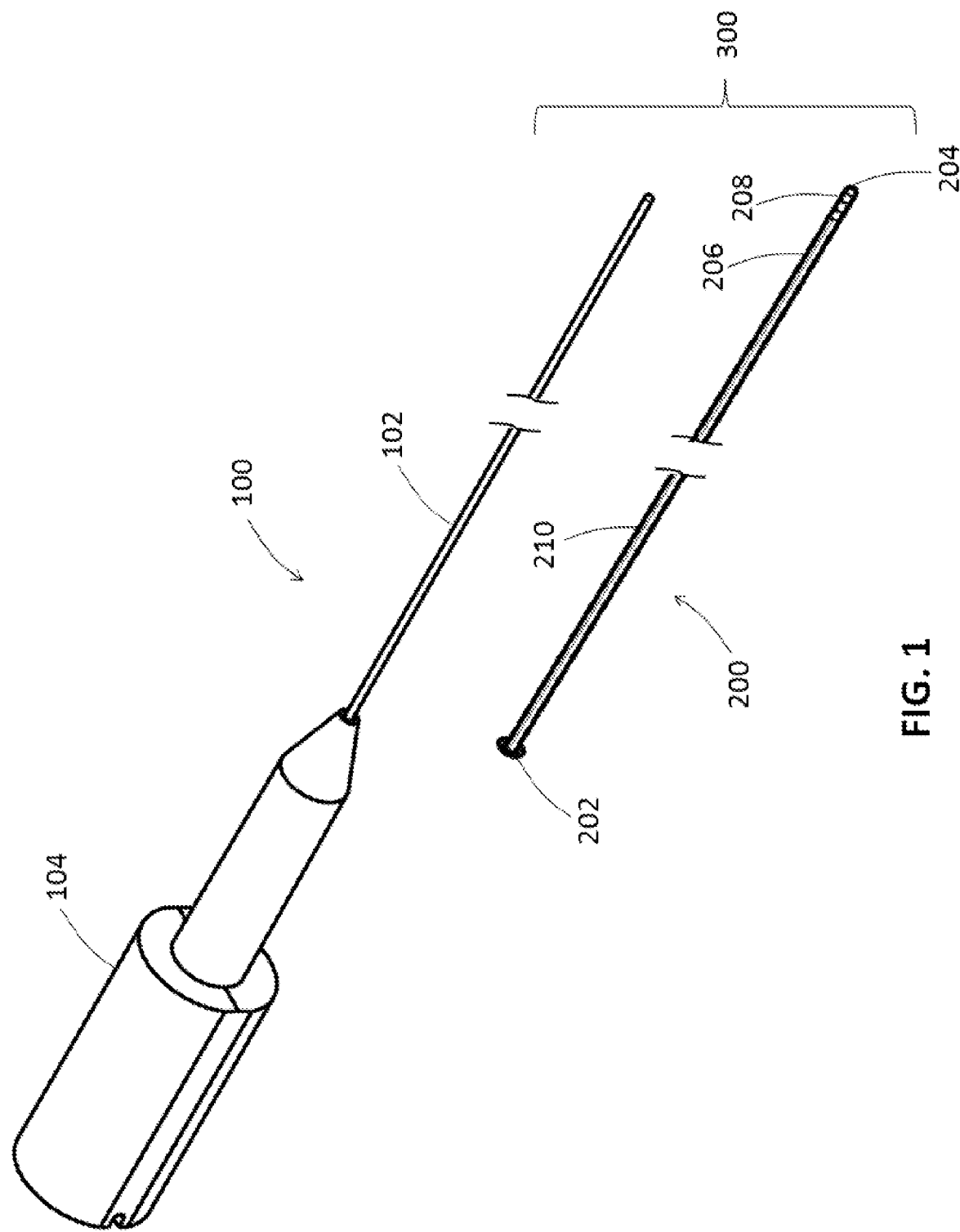
FIG. 1 is a perspective view of a first embodiment of a stylet assembly, in accordance with the disclosure.

While embodiments of the disclosure are amenable to various modifications and alternative forms, specifics thereof shown by way of example in the drawings will be described in detail. It should be understood, however, that the intention is not to limit the disclosure to the particular embodiments described. On the contrary, the intention is to cover all modifications, equivalents, and alternatives falling within the spirit and scope of the subject matter as defined by the claims.

DETAILED DESCRIPTION

Referring to FIG. 1, a custom length stylet assembly 100 for meeting medical device length requirements and tolerances, and which avoids manufacturing yield losses, is depicted in accordance with an embodiment. FIG. 1 further depicts a body implantable lead 200, which collectively with the stylet assembly 100 can be referred to as a lead kit 300. In other embodiments, a lead kit 300 may include one or more additional stylet assemblies and/or other components for aid in positioning the body implantable lead 200 to the tissue of a patient.

Figure 2A:
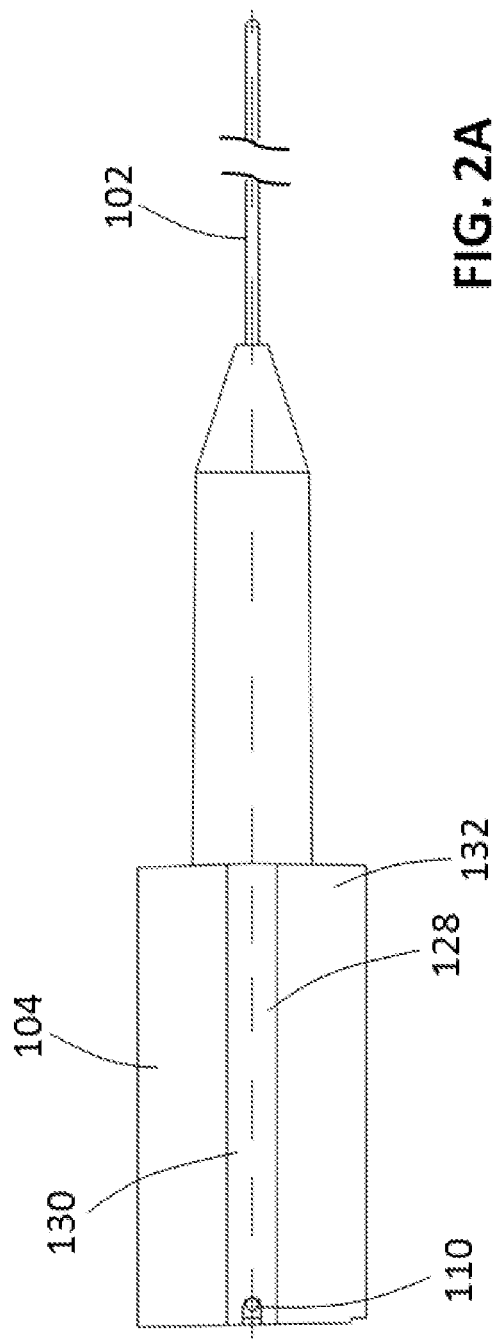
FIG. 2A is a profile view depicting the stylet assembly of FIG. 1.
Figure 2B:
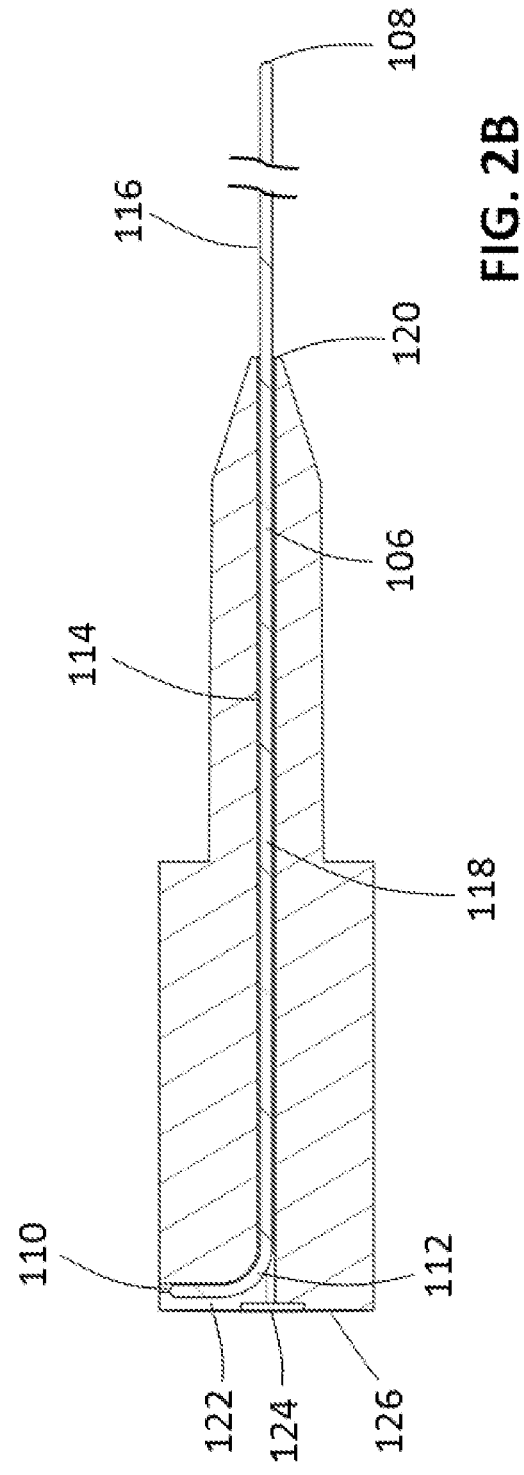
FIG. 2B is a cross-sectional view depicting the stylet assembly of FIG. 2A.
Figure 4:
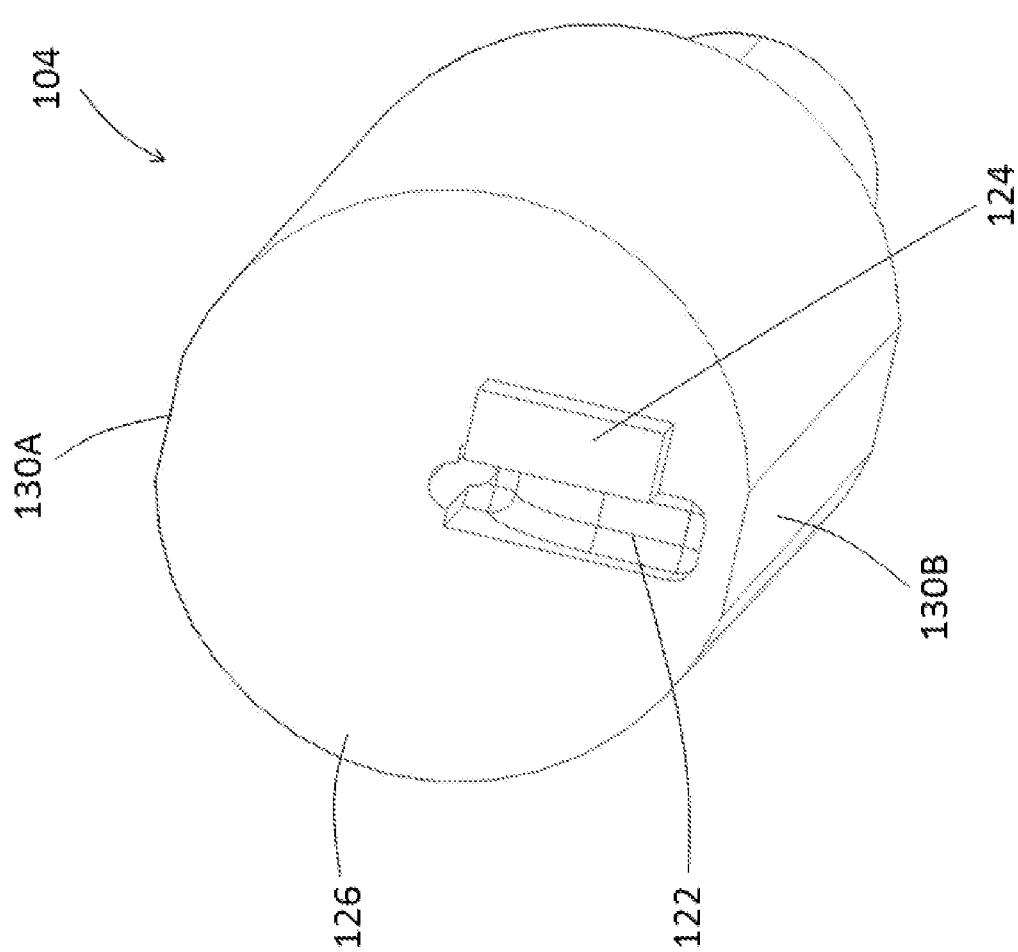
FIG. 4 is a rear perspective view depicting the stylet handle of FIG. 3A.
Figure 5:
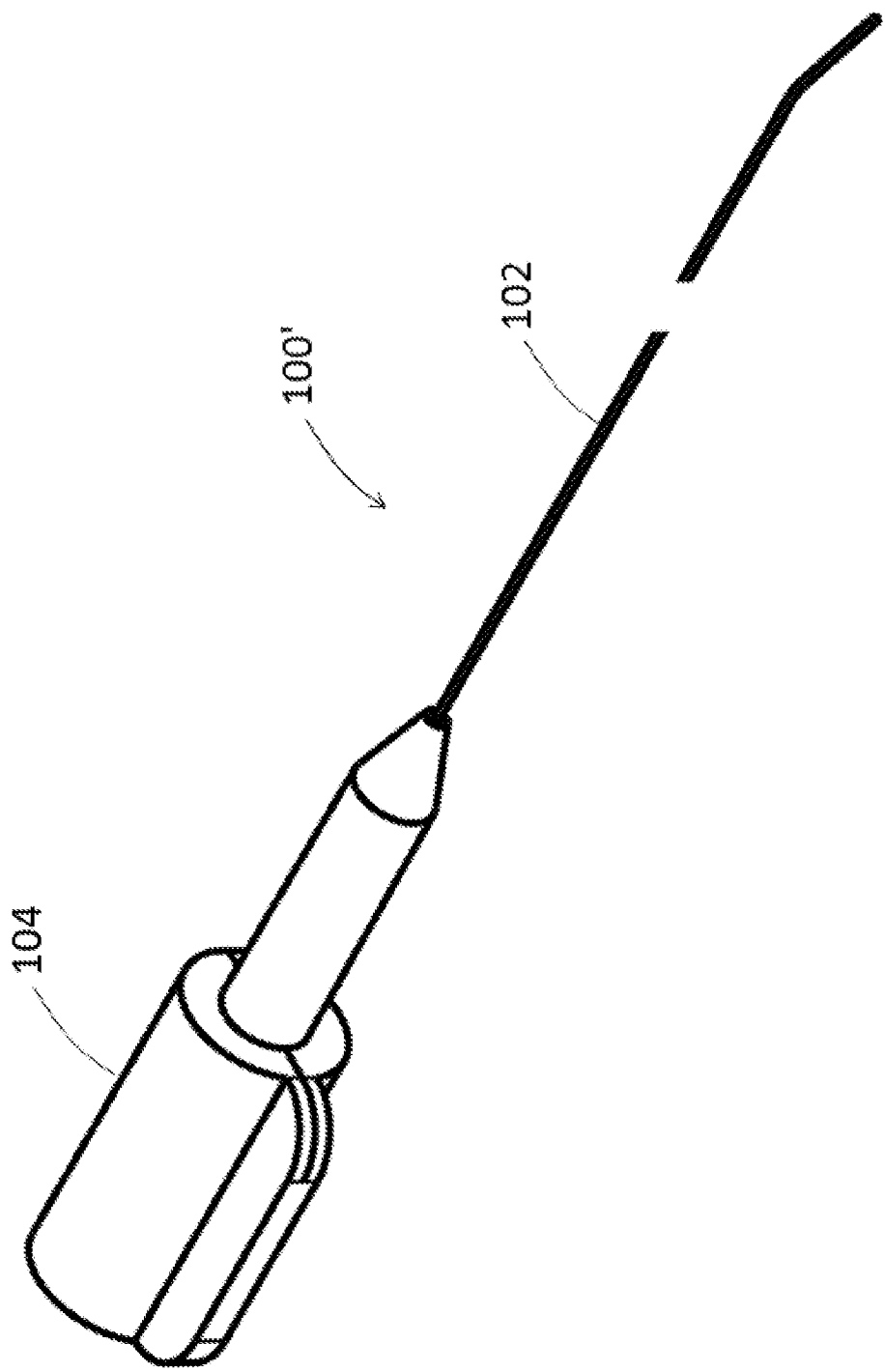
FIG. 5 is a perspective view of a second embodiment of a stylet assembly, in accordance with the disclosure.
Figure 6:
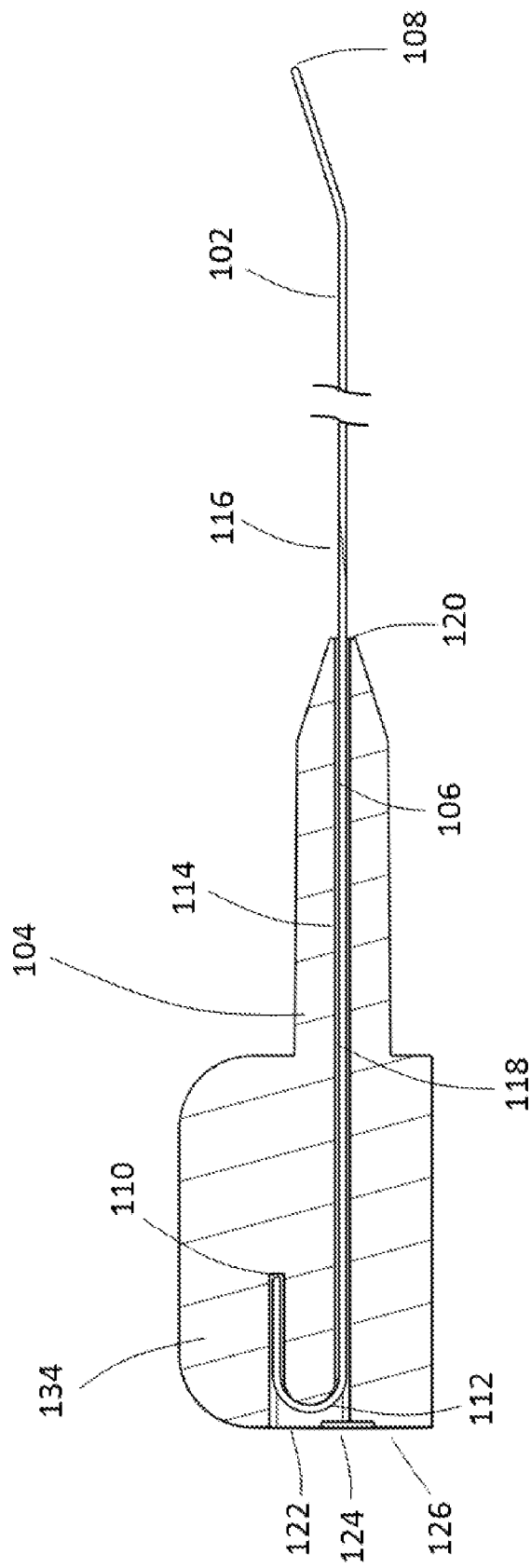
FIG. 6 is a cross-sectional view depicting the stylet assembly of FIG. 5.
Figure 7A:
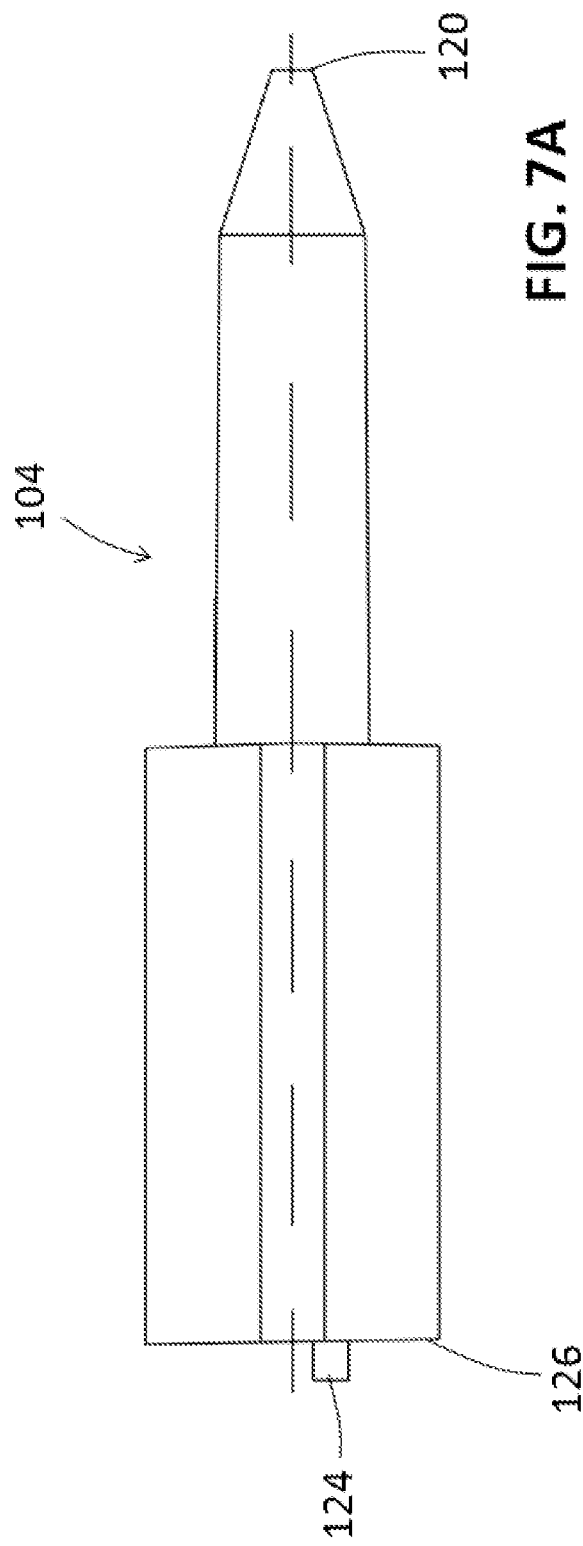
FIG. 7A is a profile view depicting a stylet handle, in accordance with an embodiment of the disclosure.
Figure 7B:
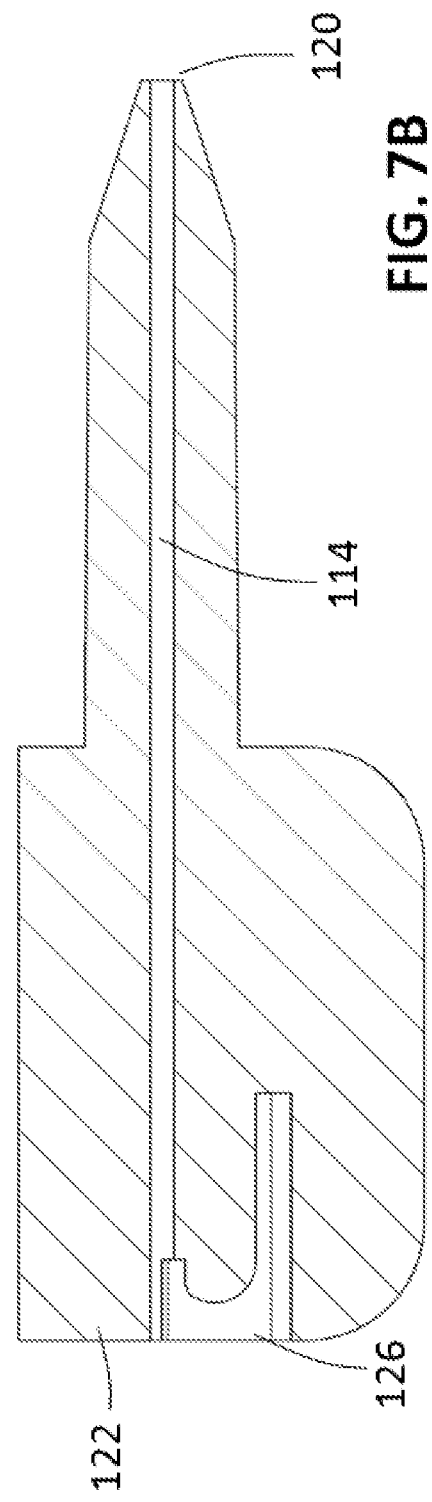
FIG. 7B is a cross-sectional view depicting the stylet assembly of FIG. 7A.
Figure 8:
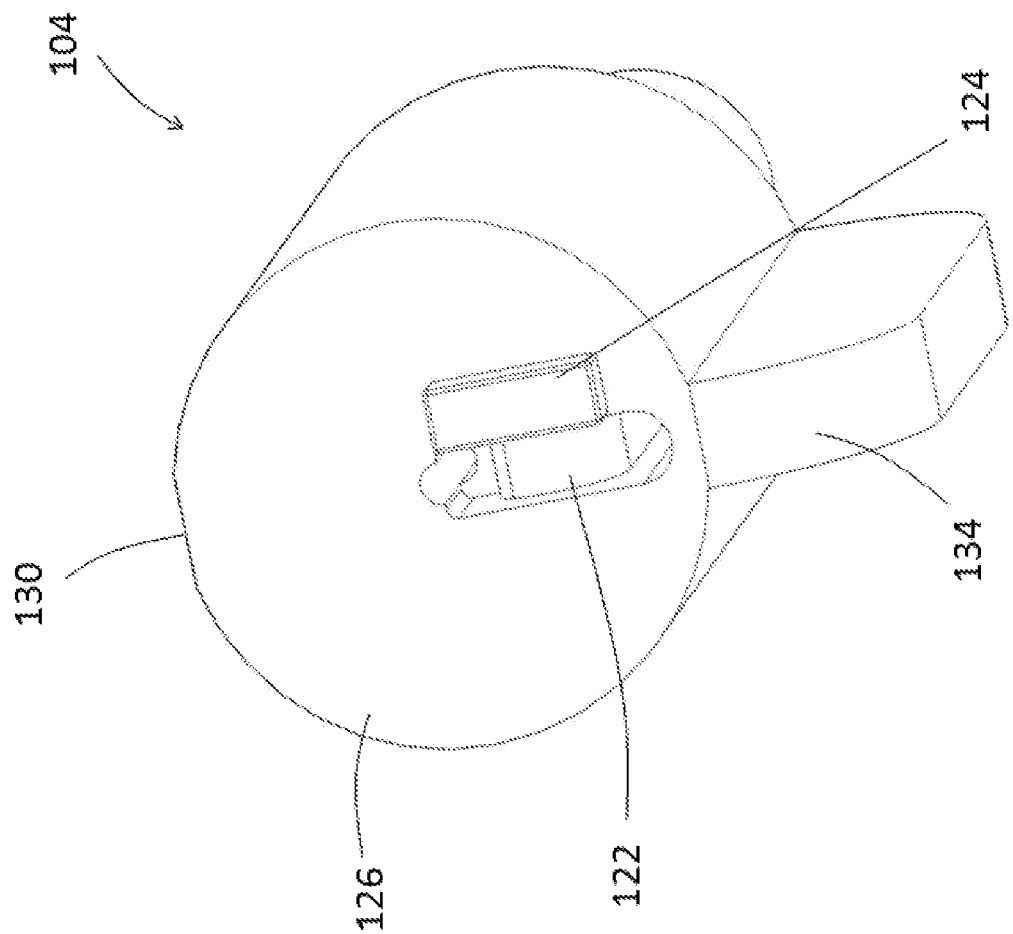
FIG. 8 is a rear perspective view depicting the stylet handle of FIG. 7A.

With additional reference to FIGS. 2A-B, in one embodiment, the stylet assembly 100 can include a stylet wire 102 and a stylet handle 104. The stylet wire 102 can include a body 106 extending between a distal end 108 and a proximal end 110 (as depicted in FIG. 2B). The stylet wire 102 can be constructed of a semi rigid, flexible wire, for example constructed of a tungsten or stainless steel alloy; although other wire construction materials are also contemplated. In some embodiments, the stylet assembly 100 can include a straight stylet wire 102 (as depicted in FIGS. 1-4). In other embodiments, the stylet assembly 100' can include one or more bends or angles defined in distal portion 108 of the stylet wire 102 (as depicted in FIGS. 5-8). A length of the stylet wire 102 can be selected to conform to a desired length. In one example, a length of the stylet wire 102 can be selected to conform to a corresponding length of the body implantable lead 200 within a predefined tolerance.

The body implantable lead 200 (depicted in FIG. 1) can be, for example, an implantable neurostimulator lead. The body implantable lead 200 can have a proximal end 202 and a distal end 204. The proximal end 202 can be configured to be operably coupled to a medical device, such as an implantable pulse generator. The distal end can be configured to be positioned in communication with body tissue of the patient for electrical stimulation thereof. In some embodiments, the body implantable lead 200 can further include one or more electrical conductors 206, electrode head 208 having one or more electrodes, and a body 210.

In some embodiments, the electrical conductor 206 can extend between the proximal end 202 and the distal end 204 of the body implantable lead 200. One or more electrodes can be affixed along the body of lead 200 and/or to the distal end 204, with appropriate with the electrical conductors 206 as needed. The electrode head 208 can be configured to be exposed to the body tissue of a patient for the supply of electrical impulses thereto. The body 210 can define a longitudinally oriented lumen extending between the proximal end 202 and a lumen termination point in proximity to the distal 204.

With additional reference to FIGS. 3A-B, the stylet handle 104 can be configured to serve as a user grip for manipulation of the stylet wire 102 during insertion and positioning of the body implantable lead 200 into a patient. The stylet handle 104 can define a longitudinally oriented throughbore 114 sized to retain a proximal portion 116 of the stylet wire 102, such that a distal portion 118 of the stylet wire 102 extends distally from a distal end 120 of the stylet handle 104. In some embodiments, the stylet handle 104 can further define a track 122 and a tab 124 (as further depicted in FIG. 4), positioned in proximity to a proximal end 126 of the stylet handle 104. In some embodiments, the stylet handle 104 can be constructed of plastic; although other construction materials are also contemplated.

In some embodiments, the stylet wire 102 can define a bent proximal portion 112. In one embodiment, the bent proximal end portion 112 has a substantially orthogonal bend of about 90°. In another embodiment, the bent proximal end portion 112 has a U-shaped bend of about 180°. Bend angles between about 0° and about 270° are also contemplated; for example, the bend can have an angle in the range of between about 45° and about 90°, or in the range of between about 90° and about 180°.

In some embodiments, the track 122 of the stylet handle 104 can be shaped and sized to retain the bent proximal end portion 112 of the stylet wire 102, when the stylet wire 102 is positioned within the longitudinally oriented throughbore 114 defined in the stylet handle 104, thereby inhibiting rotation of the stylet wire 102 relative to the stylet handle 104. In some embodiments, the tab 124, which can be positioned in close proximity to the track 122, can be melted, re-melted, reflowed or otherwise reformed to fill in the void within the track 122 surrounding the bent proximal end portion 112, thereby securely fastening the bent proximal end portion 112 within the track 122. For example, in one embodiment, the tab 124 can be melted via a soldering iron or other similar device.

In some embodiments, the stylet handle 104 can include one or more orientation members 128 configured to provide a rotational orientation reference to a user during manipulation and positioning of the body implantable lead 200 into a patient. In one embodiment, the orientation member 128 can be a flat surface 130 positioned on an otherwise cylindrical portion 132 of stylet handle 104. For example, in some embodiments, the stylet handle 104 can include a pair of opposed flat surfaces 130A/130B (as depicted in FIGS. 1-4) as an aid providing a rotational orientation reference during use.

In other embodiments, the orientation member 128 can be in the form of a keyed member 134 extending radially outward from a cylindrical portion 132 (as depicted in FIGS. 5-8). In some embodiments, the keyed member 134 can be opposite a flat surface 130 on the otherwise cylindrical portion 132 of the stylet handle 104. In some embodiments, keyed member 134 can act as an aid providing a rotational orientation reference during use.

Additionally, embodiments of orientation members 128 can also advantageously prevent unintended slippage or rotation of stylet 100, 100' in a hand of a user grasping the stylet handle 104, such as when applying a rotational torque during use of stylet 100, 100'.

In further embodiments, stylet 100 and/or 100' can be provided in, or with, a lead kit 300, which can further include a body implantable lead 200. For example, the kit 300 can comprise at least one custom length stylet device 100, and/or at least one custom length stylet device 100'. Kit 300 may be provided in whole or in part in sterile packaging, and the kit 300 can also include one or more instructions for assembly, instructions for use, the medical device which stylet 100 will be used in conjunction with, or other components configured to support user understanding of custom length stylet device 100.

Figure 9:
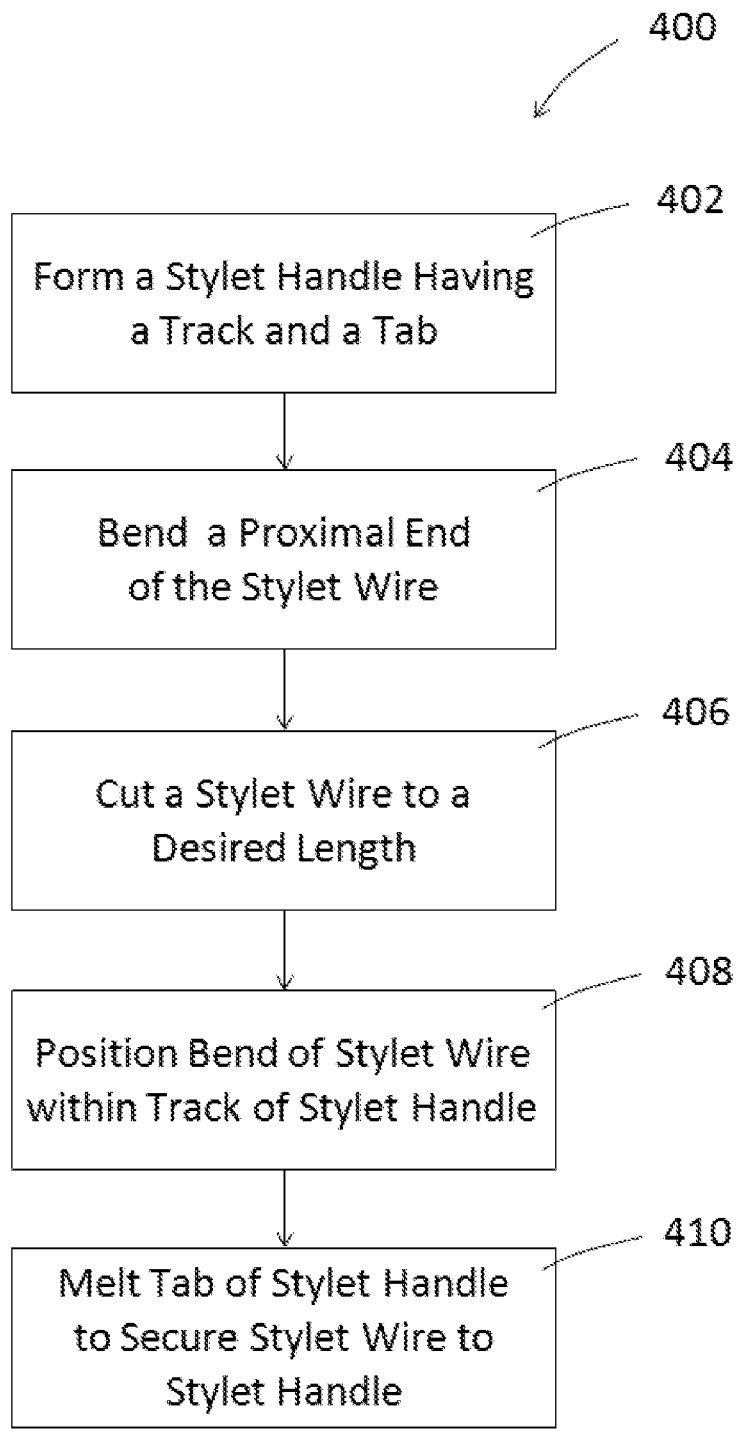
FIG. 9 is a flowchart depicting a method of assembling a stylet assembly, in accordance with an embodiment of the disclosure.

Referring to FIG. 9, a method 400 of assembling a stylet assembly 100, 100' is depicted in accordance with an embodiment of the disclosure. At 402, the stylet assembly 100, 100' can be assembled by forming a stylet handle 104 defining a longitudinally oriented through bore 114, a proximally positioned track 122, and a proximally positioned tab 124. At 404, a proximal portion 116 of the stylet wire 102 can be bent to form a bent proximal end portion 112. At 406, the stylet wire 102 can be cut to conform to a desired length, such as to corresponding to a length of a body implantable lead 200 within a predefined tolerance. At 408 proximal end portion 112 can be positioned within the track 122, such that the stylet wire 102 is positioned within the throughbore 114 and a distal portion 118 of the stylet wire 102 extends distally from a distal end 120 of the stylet handle 104. At 410, the tab 124 can be melted into the track 122, thereby securely fastening the stylet wire 102 to the stylet handle 104 and inhibiting rotation of the stylet wire 102 relative to the stylet handle 104, and thus creating stylet 100, 100' of the desired length.

It should be understood that the individual steps used in the methods of the present teachings may be performed in any order and/or simultaneously, as long as the teaching remains operable. Furthermore, it should be understood that the apparatus and methods of the present teachings can include any number, or all, of the described embodiments, as long as the teaching remains operable.

In general throughout this document, and unless otherwise noted, "proximal" is used to refer to an end or portion that is closest to the user of the device and the bent portion of the wire, and "distal" is used to refer to an end or portion that is furthest from the user of the device.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A stylet assembly for use in positioning a body implantable lead, the stylet assembly comprising:
   a stylet wire configured to extend through a lumen of the body implantable lead, the stylet wire having a length extending between a distal end and a proximal end; and
   a stylet handle configured to serve as a user grip for manipulation of the stylet wire, the stylet handle defining a longitudinally oriented throughbore sized to retain a proximal portion of the stylet wire, such that a distal portion of the stylet wire extends distally from a distal end of the stylet handle, the stylet handle further defining a proximately positioned track integrally connected to and extending from the longitudinally oriented throughbore and a tab, the track configured to retain a bent proximal end portion of the stylet wire,
   wherein the length of the stylet wire is selected during assembly of the stylet assembly to conform to a corresponding length of the body implantable lead within a predefined tolerance, and the tab of the stylet handle is arranged and configured to melt into the track to securely fasten the stylet wire to the stylet handle and inhibit rotation of the stylet wire relative to the stylet handle, wherein the stylet wire does not extend through the tab when the tab is unmelted.

2. The stylet assembly of claim 1, wherein the stylet wire is constructed of a tungsten metal alloy.

3. The stylet assembly of claim 1, wherein the bent proximal end portion of the stylet wire includes a bend of between about 45 degrees and about 90 degrees.

4. The stylet assembly of claim 1, wherein the stylet wire is constructed of a stainless steel metal alloy.

5. The stylet assembly of claim 1, wherein the bent proximal end portion of the stylet wire includes a bend of between about 90 degrees and about 180 degrees.

6. The stylet assembly of claim 1, wherein the stylet handle is constructed of plastic.

7. The stylet assembly of claim 1, wherein the stylet handle includes an orientation member configured to provide a rotational orientation reference to a user during positioning of the body implantable lead.

8. The stylet assembly of claim 7, wherein the orientation member is a flat surface positioned on an otherwise cylindrical portion of the stylet handle.

9. The stylet assembly of claim 7, wherein the orientation member is a keyed member extending radially outward from a cylindrical portion of the stylet handle.

10. The stylet assembly of claim 1, wherein the track extends from a first end in the longitudinally oriented throughbore to a second end at an outer edge of the stylet handle.

11. A lead kit for the insertion and positioning of an implantable neurostimulator lead into a body of a patient, the lead kit comprising:
  an implantable neurostimulator lead having a proximal end configured to be operably coupled to a medical device and a distal end configured to be positioned in communication with body tissue of the patient for electrical stimulation thereof, the implantable neurostimulator lead including—
    an electrical conductor extending between the proximal end and the distal end of the implantable neurostimulator lead,
    an electrode head affixed to the distal end having one or more electrodes in communication with the electrical conductor, the electrode head configured to be exposed to the body tissue for the supply of an electrical impulse thereto, and
    a body defining a longitudinally oriented lumen extending between the proximal end and a lumen termination point in proximity to the distal end; and
  a stylet assembly for use in positioning the implantable neurostimulator lead into the body of the patient, the stylet assembly including—
    a stylet wire configured to extend through the lumen of the implantable neurostimulator lead, the stylet wire having a length extending between a distal end and a proximal end; and
    a stylet handle configured to serve as a user grip for manipulation of the stylet wire, the stylet handle defining a longitudinally oriented throughbore sized to retain a proximal portion of the stylet wire, such that a distal portion of the stylet wire extends distally from a distal end of the stylet handle, the stylet handle further defining a proximately positioned track integrally connected to and extending from the longitudinally oriented throughbore and a tab, the track configured to retain a bent proximal end portion of the stylet wire,
  wherein the length of the stylet wire is selected during assembly of the stylet assembly to conform to a corresponding length of the body implantable lead within a predefined tolerance, and the tab of the stylet handle is arranged and configured to melt into the track to securely fasten the stylet wire to the stylet handle and inhibit rotation of the stylet wire relative to the stylet handle, wherein the stylet wire does not extend through the tab when the tab is unmelted.

12. The lead kit of claim 11, wherein the stylet wire is constructed of a tungsten metal alloy.

13. The lead kit of claim 11, wherein the bent proximal end portion of the stylet wire includes a bend of between about 45 degrees and about 90 degrees.

14. The lead kit of claim 11, wherein the stylet wire is constructed of a stainless steel metal alloy.

15. The lead kit of claim 11, wherein the bent proximal end portion of the stylet wire includes a bend of between about 90 degrees and about 180 degrees.

16. The lead kit of claim 11, wherein the stylet handle is constructed of plastic.

17. The lead kit of claim 11, wherein the stylet handle includes an orientation member configured to provide a rotational orientation reference to a user during positioning of the body implantable lead.

18. The lead kit of claim 17, wherein the orientation member is a flat surface positioned on an otherwise cylindrical portion of the stylet handle.

19. The lead kit of claim 17, wherein the orientation member is a keyed member extending radially outward from a cylindrical portion of the stylet handle.

20. The lead kit of claim 11, wherein the track extends from a first end in the longitudinally oriented throughbore to a second end at an outer edge of the stylet handle.

* * * * *